United States Patent
Johnstone (10) Patent No.: US 7,347,861 B2
(45) Date of Patent: Mar. 25, 2008

(54) BONE FIXTURE APPARATUS AND JIG (75) Inventor: Alan Johnstone, Aberdeen (GB)

(73) Assignee: Grampian Health Board (GB)

( * ) Notice: Subject to any disclaimer, the term of this patent is extended or adjusted under 35 U.S.C. 154(b) by 6 days.

(21) Appl. No.: 10/470,507

(22) PCT Filed: Jan. 31, 2002

(86) PCT No.: PCT/GB02/00423

§ 371 (c)(1),
(2), (4) Date: Dec. 30, 2003

(87) PCT Pub. No.: WO02/060331

PCT Pub. Date: Aug. 8, 2002

(65) Prior Publication Data

US 2004/0122428 A1 Jun. 24, 2004

(30) Foreign Application Priority Data

Jan. 31, 2001 (GB) .................. 0102488.4

(51) Int. Cl.
*A61B 17/58* (2006.01)
(52) U.S. Cl. ..................................... 606/62
(58) Field of Classification Search ........... 606/62–68, 606/86–89, 96–98
See application file for complete search history.

(56) References Cited

U.S. PATENT DOCUMENTS

| 4,281,649 | A | * | 8/1981 | Derweduwen | 606/64 |
|---|---|---|---|---|---|
| 4,644,943 | A | * | 2/1987 | Thompson et al. | 606/64 |
| 4,776,330 | A | | 10/1988 | Chapman et al. | |
| 4,913,137 | A | * | 4/1990 | Azer et al. | 606/64 |
| 4,946,459 | A | | 8/1990 | Bradshaw et al. | |
| 5,403,322 | A | | 4/1995 | Herzenberg et al. | |
| 5,454,813 | A | * | 10/1995 | Lawes | 606/62 |
| 5,531,748 | A | * | 7/1996 | de la Caffiniere | 606/62 |
| 5,928,235 | A | * | 7/1999 | Friedl | 606/64 |
| 6,010,505 | A | * | 1/2000 | Asche et al. | 606/62 |
| 6,221,074 | B1 | * | 4/2001 | Cole et al. | 606/62 |
| 6,379,360 | B1 | * | 4/2002 | Ackeret et al. | 606/67 |
| 6,692,496 | B1 | | 2/2004 | Wardlaw | |

FOREIGN PATENT DOCUMENTS

| DE | 87 12 991 A1 | 11/1987 |
|---|---|---|
| EP | 0 903 112 A1 | 3/1999 |
| FR | 2 385 378 A1 | 10/1978 |
| FR | 2 690 330 A1 | 10/1993 |
| WO | WO-01/56487 A1 | 8/2001 |

* cited by examiner

*Primary Examiner*—Eduardo C. Robert
*Assistant Examiner*—Michael J. Araj
(74) *Attorney, Agent, or Firm*—Lerner, David, Littenberg, Krumholz & Mentlik, LLP (57) ABSTRACT

A bone fixture apparatus has an elongate fixture device intended to be inserted in a metaphysical region of a long bone. The device is inserted generally transversely of the direction of the medullary cavity in the bone. The fixture device includes an aperture extending laterally thereof and intended to accommodate an intramedullary nail inserted longitudinally therethrough into the cavity. The fixture device is further formed with an axial aperture intended to receive a securing element capable of insertion therein to firmly engage said nail with the fixture device. Also disclosed is a jig arrangement for locating, relative to a long bone, the bone fixture apparatus.

16 Claims, 10 Drawing Sheets

BONE FIXTURE APPARATUS AND JIG

BACKGROUND OF THE INVENTION

This invention relates to bone fixture apparatus for use in stabilising fractures at or near the metaphyses of long bones, and to jigs for use in connection therewith or separately.

Techniques based upon the use of intramedullary nails are well established for stabilizing fractures in long bones, and such techniques are valuable in many respects, in particular because they require minimal surgery adjacent the bone to be treated. Their usefulness, however, is mainly restricted to the treatment of fractures located intermediate the metaphyseal regions, and in which there is little fracture damage running longitudinally of the bone.

This invention aims, inter alia, to render intramedullary nail technology suitable for use in the treatment of fractures at or near metaphyseal regions of long bones.

SUMMARY OF THE INVENTION

According to the invention from one aspect, there is provided a bone fixture apparatus for application to a metaphyseal region of a long bone, the apparatus comprising an elongate fixture device intended to be inserted, in the region, generally transversely of the direction of the medullary cavity in said bone; wherein the fixture device includes an aperture extending laterally thereof and intended to accommodate an intramedullary nail inserted longitudinally therethrough into said cavity, and wherein said fixture device is further formed with an axial aperture intended to receive a securing element capable of insertion therein to firmly engage the said nail with the fixture means.

The fixture device may conveniently comprise a bolt-like, screw-like or nail-like member intended for insertion into a pre-drilled passage in the bone and to engage with cancellous bone to provide a secure fixture which assists in stabilizing a fracture and provides a rigid mount for the intramedullary nail.

In one preferred embodiment of the invention, the fixture device comprises a bolt-like member including first and second hollow, cylindrical components of different diameter inserted coaxially into the bone from opposite directions and adapted to interfit, within the bone, in any convenient manner so as to be capable of asserting stabilising forces laterally of the long bone under treatment.

In this embodiment, either or both of the hollow, cylindrical components of the bolt-like member may be formed with an nail-receiving aperture, extending transversely of the cylinder axes and intended to accommodate an intramedullary nail inserted therethrough into the medullary cavity of the bone. Moreover, one or both of the cylindrical components is formed with an axially extending aperture, preferably screw-threaded, into which a locking device, such as a grub screw, may be inserted and tightened against an intramedullary nail, disposed in said nail-receiving aperture, to securely fix the nail to the bolt-like fixture means.

In another preferred embodiment, the fixture device comprises a screw-like member, inserted from only one side of the bone but otherwise with generally the same disposition, with respect to the bone, as the bolt-like device described previously. In this embodiment, it is essential for the screw-like component to engage, with its screw-threaded distal end, into cancellous bone in order to provide a firm fixture base. As with the previous embodiment, the screw-like member is formed with a nail-receiving aperture, extending transversely of its longitudinal axis, through which an intramedullary nail can be inserted. The nail can be firmly secured to the screw-like member, as before, by means of a locking device, such as a grub screw, inserted into a suitable bore running axially of the screw-like member.

In yet another preferred embodiment of the invention, the fixture device comprises a finned nail-like member, the finned, and sharpened distal end of which is intended to be embedded, by conventional means, in cancellous bone. The remaining features of the nail-like member are similar to those of the screw-like member.

Another object of the invention is to provide jig arrangements which, inter alia, are capable of accurately locating incision and boring positions required as a precursor to the insertion, into the bone, of the bone fixture apparatus of the first aspect of the invention.

In accordance with this object of the invention there is provided a jig arrangement for locating a bone fixture apparatus relative to a long bone, the jig arrangement comprising an elongate rod member with an intramedullary probe releasably attached to an end thereof and in axial alignment therewith; the rod member being provided, in the vicinity of its attachment to said probe, with a shoulder intended to engage with an external bone surface when the probe is inserted into the medullary cavity of the bone; said rod member then acting as a core guide for a hollow sleeve member, also forming part of said jig arrangement, intended to be inserted over said rod member and bearing a guide portion at least partially encircling said bone and formed with at least one aperture extending transversely with respect to the axes of the rod member and the probe and intended to guide a drilling means for drilling in said bone a bore to accommodate a component of the bone fixture apparatus.

BRIEF DESCRIPTION OF THE DRAWINGS

In order that the invention may be clearly understood and readily carried into effect, certain embodiments thereof will now be described, by way of example only, with reference to the accompanying drawings, of which.

DETAILED DESCRIPTION

Figure 1:
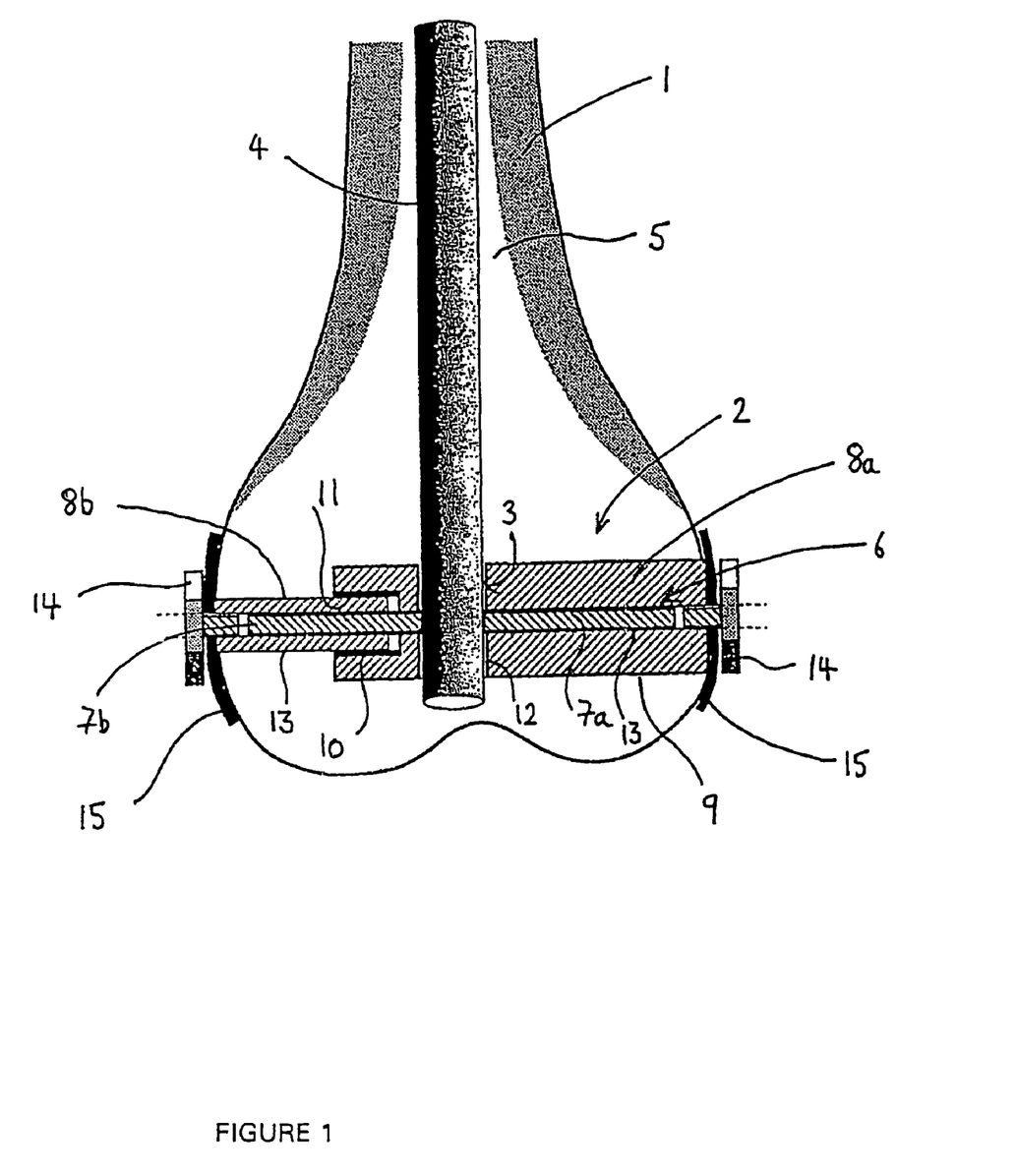
FIG. 1 shows, in cross-section, a bone fixture apparatus in accordance with a first embodiment of the invention.

Referring to FIG. 1, there is shown a bone fixture apparatus in accordance with a first embodiment of the invention, as applied to a metaphyseal region of a long bone 1. The apparatus of this embodiment comprises an elongate fixture device, indicated at 2, intended to be inserted generally transversely of the direction of the medullary cavity of the bone 1. The fixture device 2 includes an aperture 3 extending laterally thereof and intended to accommodate an intramedullary nail 4 inserted longitudinally therethrough into the medullary cavity 5 of the bone 1, and the fixture device 2 is further formed with an axial aperture 6 intended to receive a securing element 7 capable of insertion therein to firmly engage the nail 4 with the fixture means 2.

The fixture device in this embodiment comprises a bolt-like, member 8 intended for insertion into a pre-drilled-passage 9 in the bone 1 and to engage with cancellous bone to provide a secure fixture which assists in stabilising a fracture and provides a rigid mount for the intramedullary nail 4.

In particular, in this first embodiment of the invention, the bolt-like member 8, constituting the fixture device 2, includes first and second hollow, cylindrical components 8a, 8b of different diameter inserted coaxially into the bone 1 from opposite directions and adapted to interfit, within the bone, so as to be capable of asserting stabilising forces laterally of the long bone under treatment. In this example, the components 8a and 8b interfit by screw fitments, the larger diameter component 8a being formed with a screw-threaded bore 10 which engages with an external screw thread 11 formed on the outer surface of the smaller diameter component 8b; the screw threading being provided at least in the vicinity of the distal end of the component 8b.

As an alternative to the use of screw threading for the interfitting between components 8a and 8b, any suitable alternative arrangement can be used, such as bayonet fixtures or splined fixtures, bearing in mind that it is desired that the fixture device 2 shall provide sufficient force, directed laterally of the bone 1, to stabilise a fracture in the vicinity of the metaphyseal region thereof.

Either or both of the hollow, cylindrical components 8a, 8b of the bolt-like member may contain the nail-receiving aperture 3, extending transversely of the axes of the cylindrical components and intended to accommodate an intramedullary nail 4 inserted therethrough into the medullary cavity of the bone. In this example, the larger diameter component 8a is formed with a lateral throughbore 12 which constitutes the nail receiving aperture 3 in its entirety.

Moreover, one or both of the cylindrical components 8a, 8b is formed with a screw-threaded, axially extending aperture 13, constituting the axial aperture 6, into which securing elements, such as grub screws 7a, 7b, may be inserted and tightened against the intramedullary nail 4, when disposed in the nail-receiving aperture 12, to securely fix the nail 4 to the bolt-like fixture means 8.

In some circumstances, depending upon factors such as the nature of the fracture, the state of health of the bone itself and the diameter of the components of the fixture means 8, it can be advantageous to employ, between the bone 1 on the one hand, and the heads 14 of one or both of the component parts 8a and 8b of the fixture means 8 on the other hand, washer-type plates 15 to perform a load-spreading function.

The heads 14 may be integrally formed with the respective components 8a, 8b, or they may be separately formed and screwed into the threaded bores 13 after the grub screws 7a, 7b have been fitted therein. If this construction is adopted, however, the proximal end of the bore 13 of one or both components 8a, 8b should be suitably keyed so that the components can be relatively manipulated to permit their interfitment as described above.

Figure 2:
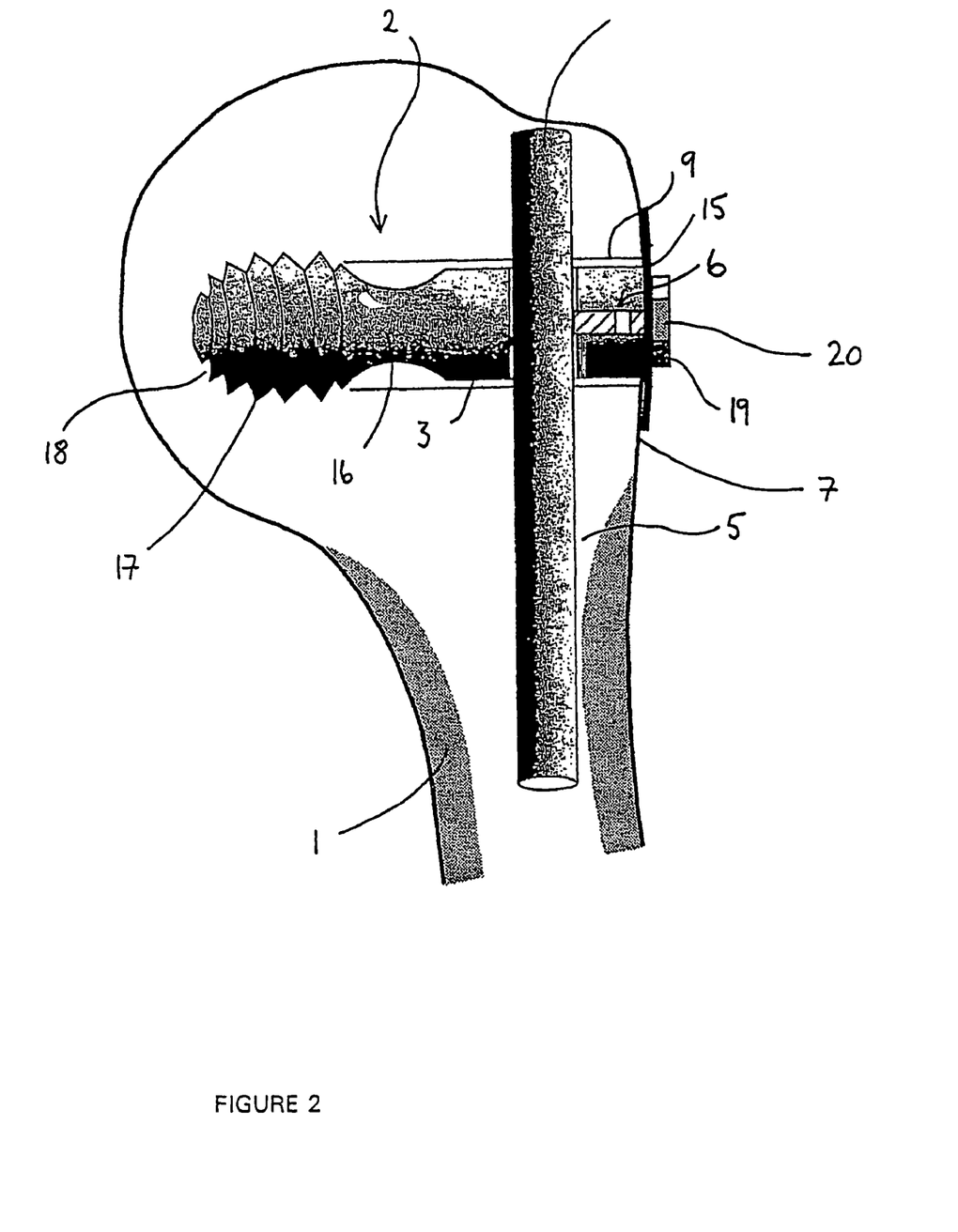
FIG. 2 shows, in cross-section, a bone fixture apparatus in accordance with a second embodiment of the invention.

Referring now to FIG. 2, there is shown a second embodiment of the invention, in which the fixture device 2 comprises a screw-like member 16, for example a lag screw, inserted from only one side of the bone but otherwise with generally the same disposition, with respect to the bone, as the bolt-like device 8 described with reference to FIG. 1. In this embodiment, it is essential for the screw-like component 16 to engage, with its screw-threaded distal end 17, into cancellous bone 18 in order to provide a firm fixture base. As with the embodiment of the invention described with reference to FIG. 1, the screw-like member 16 is formed with a nail-receiving aperture 3, extending transversely of its longitudinal axis, through which an intramedullary nail 4 can be inserted. The nail 4 can be firmly secured to the screw-like member 16, as described with reference to FIG. 1, by means of a locking device, such as a grub screw 7, inserted into a suitable bore 6 running axially of the screw-like member 16.

It will be appreciated that the proximal end 19 of the screw-like member 16 is suitably keyed to permit the member 16 to be engaged, in any convenient, known manner, with the cancellous bone 18, using conventional tools. As described previously, a load-spreading washer-type plate 15 can be used against the bone surface, being held in place by means of a cap member 20 screw-fitted into the bore 6.

Figure 3:
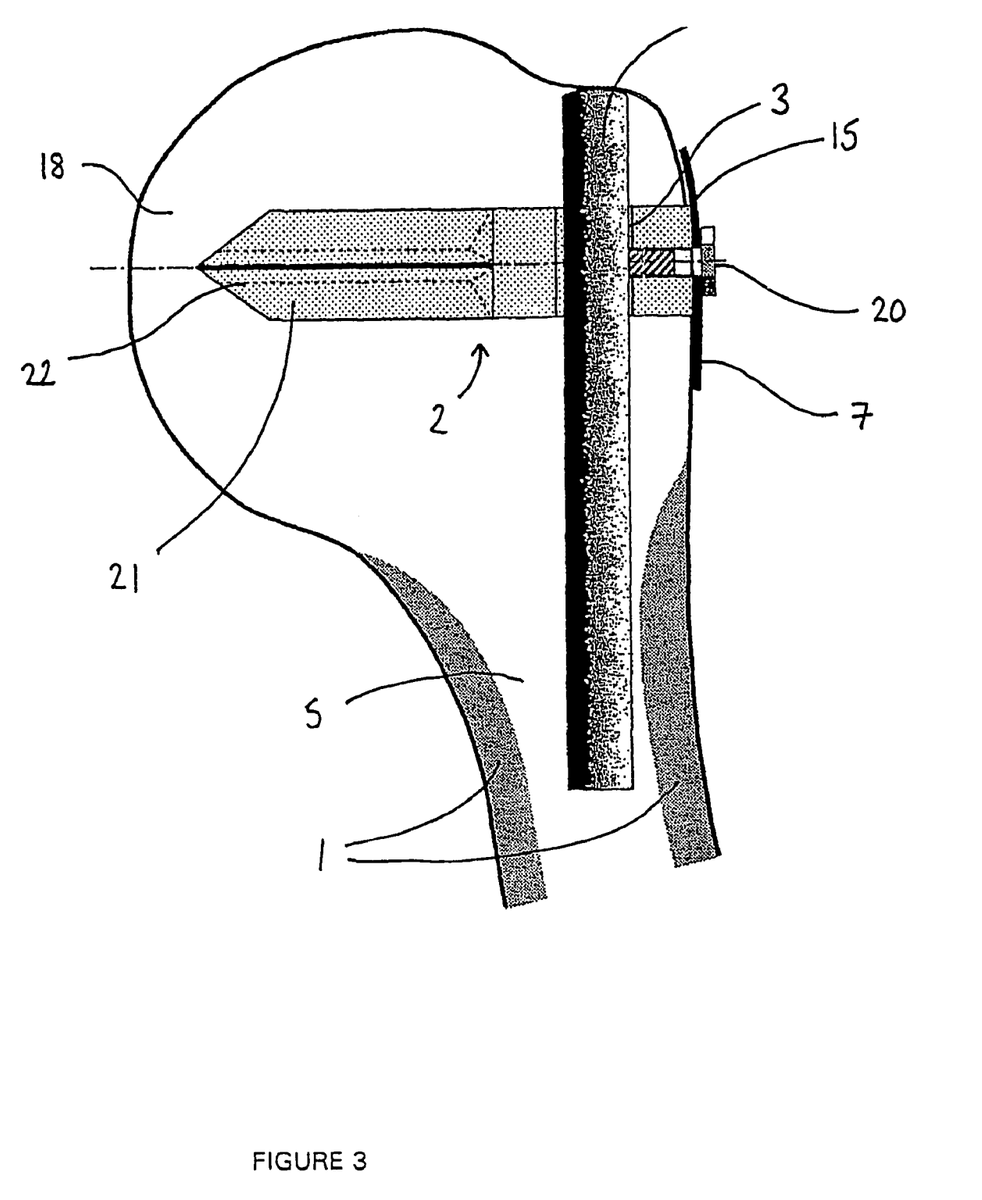
FIG. 3 shows, in cross-section, a bone fixture apparatus in accordance with a third embodiment of the invention.
Figure 4A:
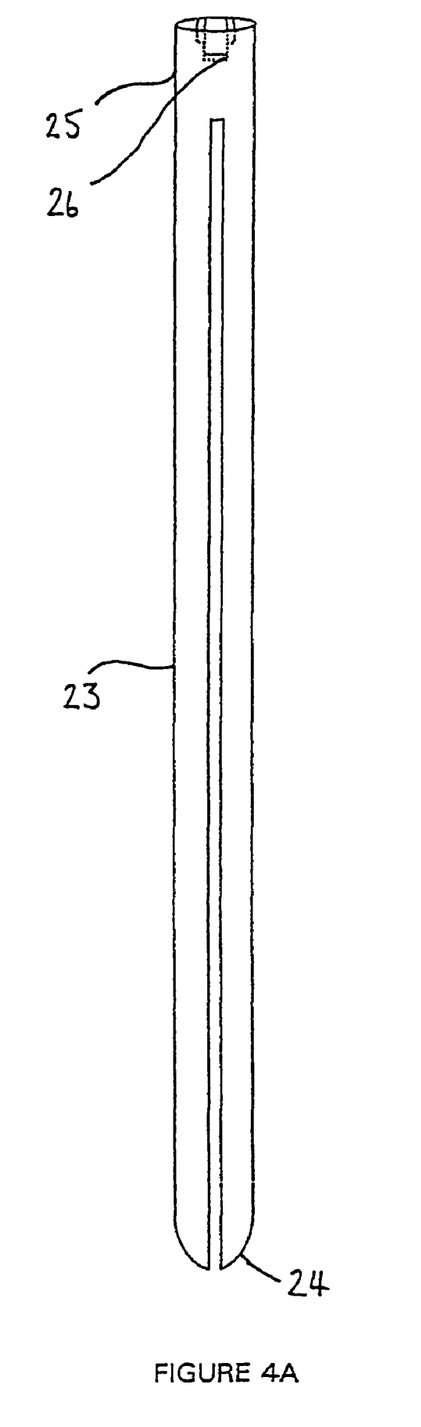
FIGS. 4(a) and 4(b) show respective side views, relatively displaced by 90 degrees, of an intramedullary probe used in conjunction with jig arrangements according to certain embodiments of the second aspect of the invention.
Figure 4B:
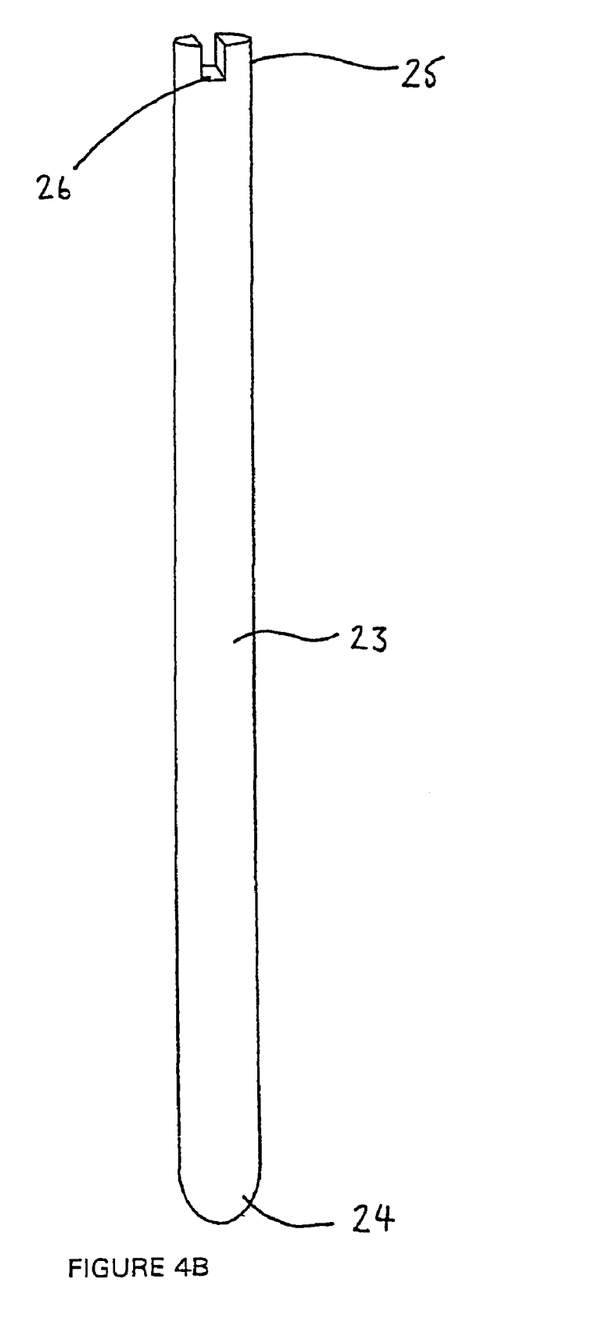

Referring now to FIG. 3, a third embodiment of the invention will be described, in which the fixture device 2 comprises a finned, nail-like member 21, the finned, and sharpened distal end 22 of which is intended to be embedded, by conventional means, in cancellous bone 18. The remaining features of the nail-like member 21 are similar to those of the screw-like member 16 described with reference to FIG. 2, and will thus not be further described herein.

In order to accurately locate the fixture device 2 of any of the foregoing embodiments of the invention in relation to the bone to which they are to be affixed, it is preferable to utilize a jig arrangement of the kind to be described with reference to the following FIGS. 4 to 10.

A common element of the preferred jig arrangements now to be described is the use of a preliminary intramedullary device 23, which will hereinafter be referred to as a probe since it is intended to enter, temporarily and for alignment purposes, into the intramedullary cavity. The probe 23 is withdrawn from the cavity once the necessary alignment procedures have been completed and the holes necessary to accommodate the fixture device have been drilled, and is later to be replaced by the intramedullary nail 4. The probe 23 is shown (inter alia) in FIGS. 4a and 4b, which are side views from orthogonal directions, and it will be seen that it comprises an elongate rod, slotted from its distal end 24 through most of its length. At the proximal end 25 of the probe 23 is an axially disposed bore hole 26 which is screw threaded, or otherwise provided for interfitment with the remaining components of the jig arrangement.

Figure 5:
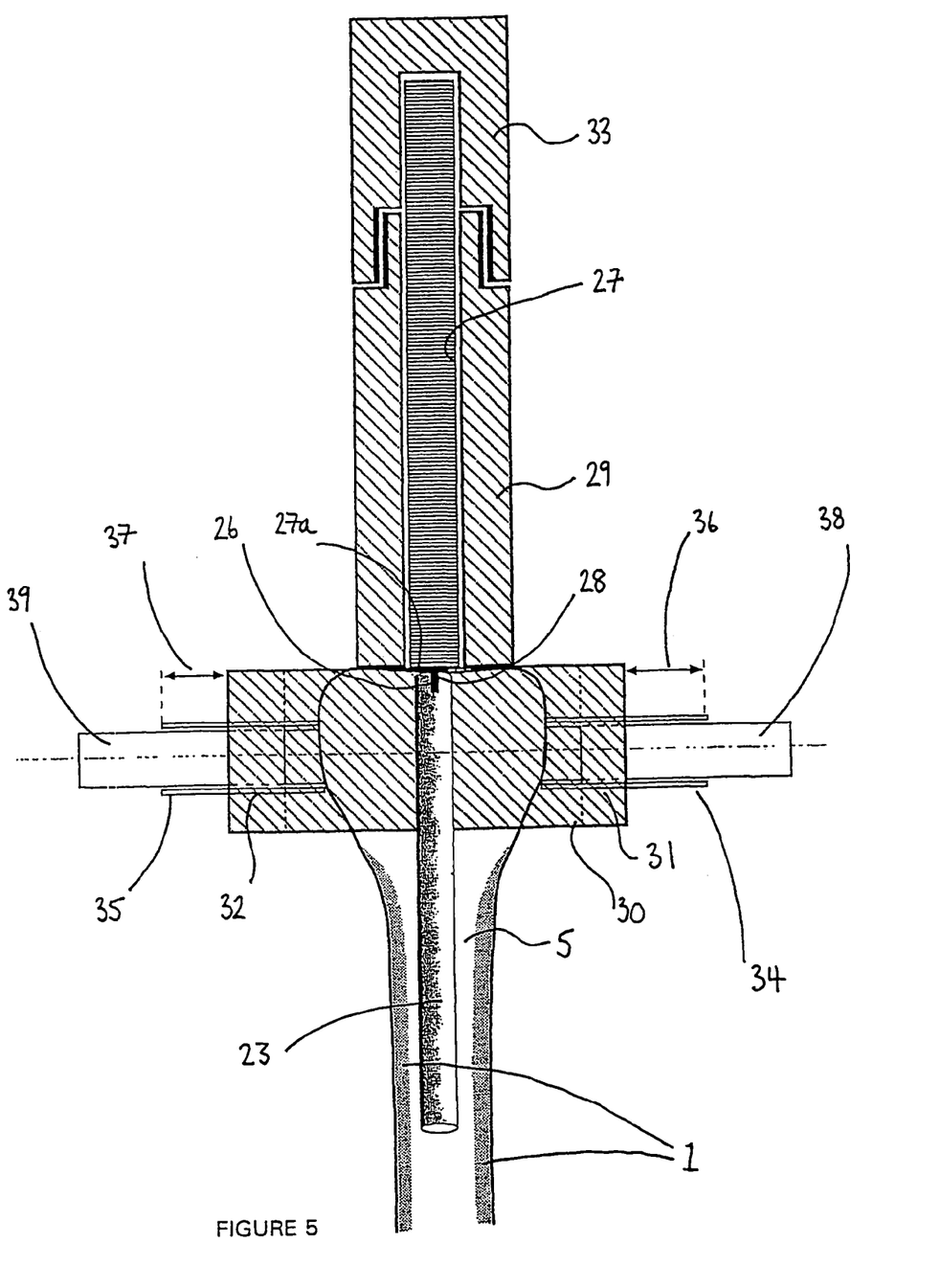
FIGS. 5, 6 and 7 show respective views of a jig arrangement for use with the first embodiment of a bone fixture apparatus, in accordance with the invention, described with reference to FIG. 1.
Figure 6:
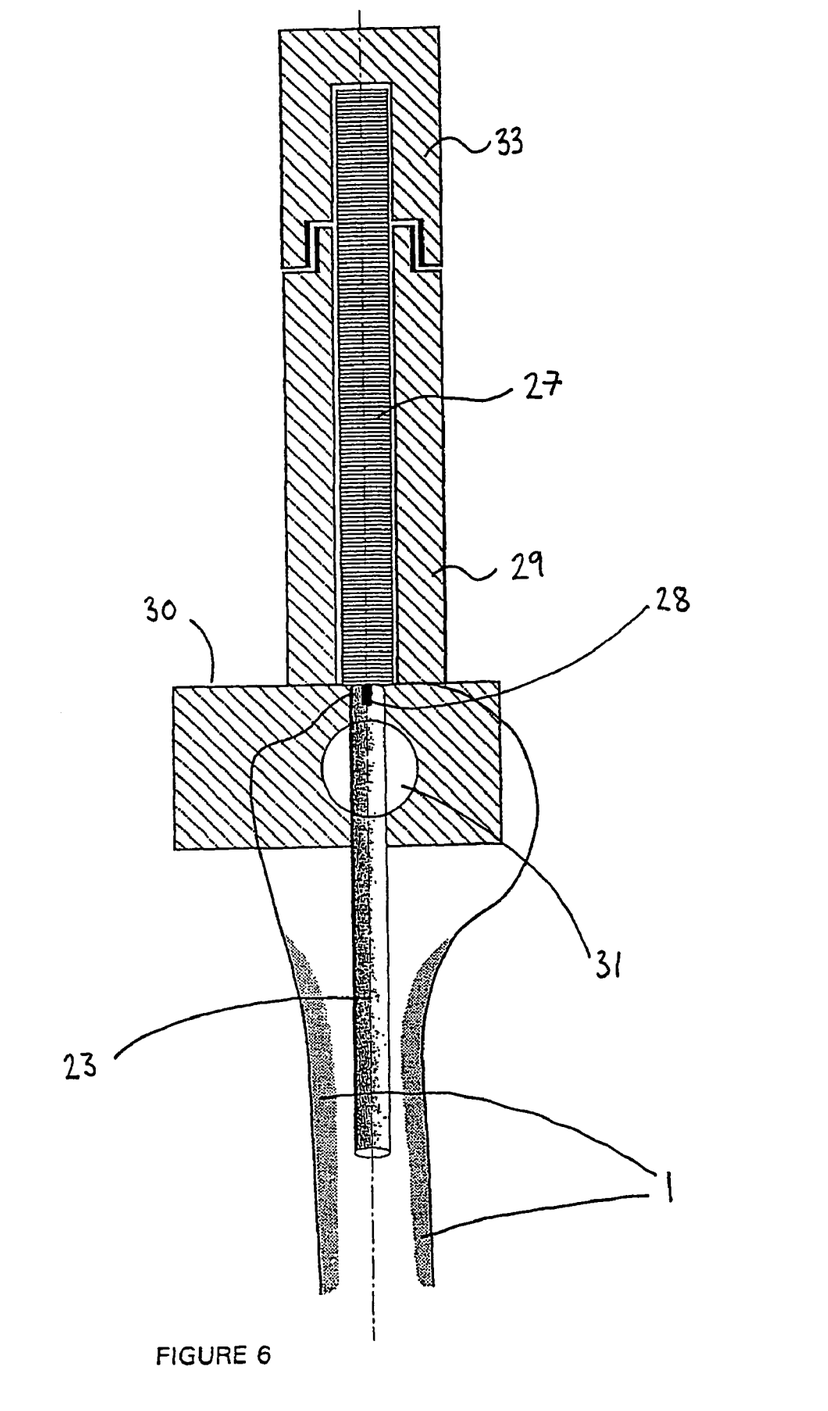
Figure 7:
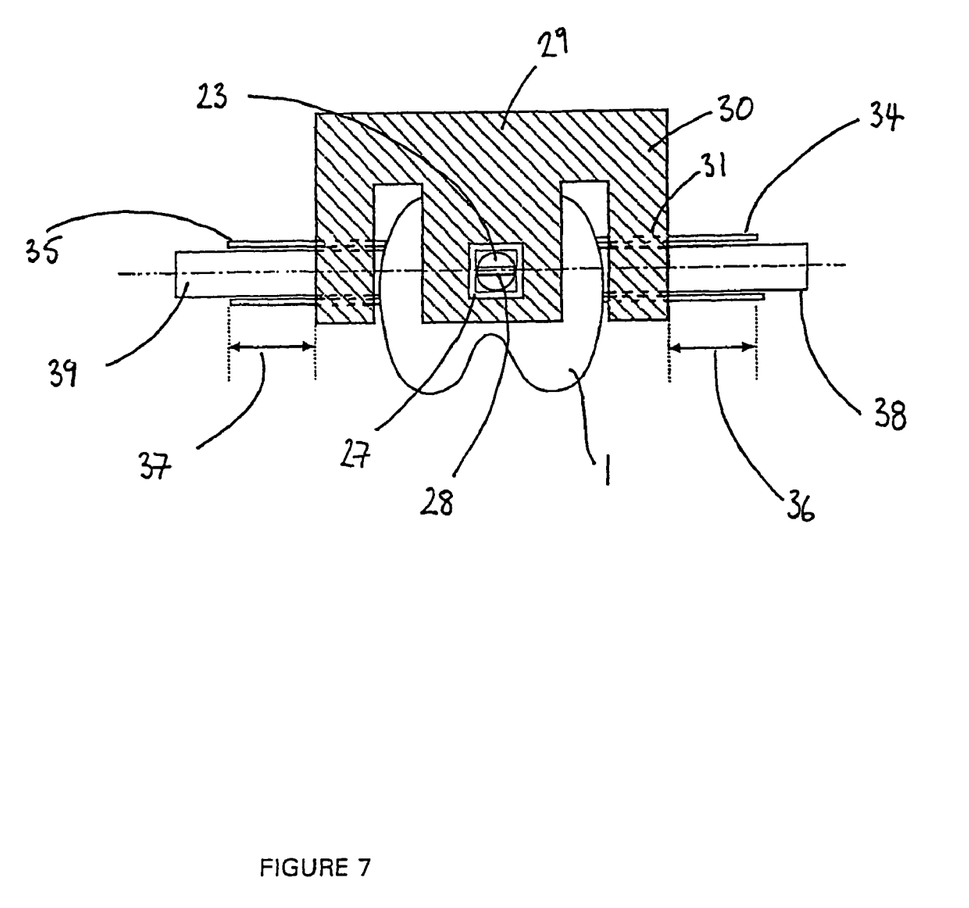

Referring now to FIGS. 5, 6 and 7, which show a jig arrangement for use in connection with the embodiment of the invention described with reference to FIG. 1, a first component of the jig comprises an elongate rod member 27 with the probe 23 releasably attached to its distal end, in axial alignment with the rod member 27, by means of a screw 28 protruding axially from the end of the rod member 27 and engaging in the screw-threaded bore 26 formed in the proximal end of probe 23. The rod member 27 is preferably of squared cross-section, and is provided, in the vicinity of its attachment to the probe 23, with a shoulder 27a intended to engage with an external surface of the bone 1 when the probe 23 is inserted into the medullary cavity 5 of the bone 1. The rod member 27 acts as a core guide for a second component of the jig arrangement, which comprises a hollow sleeve member 29 intended to be inserted coaxially over the rod member 27.

The sleeve member 29 bears a guide portion 30 configured and positioned so as to extend to either side of the bone 1 and formed with a pair of apertures 31 and 32 extending transversely with respect to the axes of the rod member 27 and the probe 23, and intended to guide a drilling means (not shown) of conventional kind used for drilling, in said bone, the bore-like passage 9 (see FIG. 1) to accommodate the bone fixture device 8 of the bone fixture apparatus 2. In this example, the guide portion 30 is of yoke-like form, containing a pair of limbs extending to either side of the bone. In alternative constructions, the guide portion 30 may be of arcuate form, and dimensioned to encircle or partially encircle the subject bone area.

A third jig component, comprising a cap member 33, is used to retain the jig components 27 and 29 in stable and fixed inter-relationship during the jigging operation. The cap member 33 may be screw-fitted or otherwise securable to the proximal end of rod member 27 so as to hold the sleeve member 29 in place.

At least the major components of the jig arrangement, such as the rod member 27, the sleeve member 29, the probe 23 and possibly also the cap member 33, are preferably radiolucent so that radiographic techniques can be applied where necessary to permit positioning and alignment of critical features and components to be checked.

In operation, and assuming that a longitudinal metaphyseal fracture exists, it is to be expected that most surgeons will prefer to reduce and hold the major metaphyseal fracture fragments by percutaneous means prior to gaining access to the medullary canal of the long bone in conventional manner. At this stage, the surgeon may prefer to use a guide wire prior to reaming the intramedullary canal to accommodate the correct diameter of probe (such as 23) or alternatively ream the canal by hand. This done, a probe 23 of appropriate length and diameter is attached to the rod member 27 of the jig arrangement and inserted into the medullary canal until the shoulder 27*a* abuts the end of the bone. Once in place, the sleeve member 29 is slotted over the rod member 27 and the cap member 33 screwed or otherwise fixed into place, ensuring that the three components 27, 29 and 33 are locked together as one, providing optimal placement of metaphyseal and diaphyseal implants.

Short incisions, down to bone, are made over the medial and lateral metaphyseal cortices, and the overlying soft tissue parted using a periosteal elevator. Securing sleeves 34 and 35 respectively are screwed into position within the bore-aligning apertures 31 and 32 formed in the guide portion 30 of the sleeve member 29 to lie on the outer aspect of the medial and lateral cortices of the metaphyseal fragments and thereby maintain reduction of the fracture. Once the jig components are all secured in place, it is possible to accurately estimate the length of the bolt components 8*a* and 8*b* (see FIG. 1) required to achieve fixation due to the inclusion, on the outer aspect of the securing sleeves 34 and 35 respectively, of measuring gauges 36 and 37 which can be read as to their displacement relative to the outer rims of the apertures 31 and 32 respectively.

Guide drill sleeves 38, 39 permitting the surgeon to accurately place a guide wire across the metaphys are inserted respectively into the apertures 31 and 32 and, after checking the position using an image intensifier, the probe 23 is removed and the appropriate diameter of drill inserted taking into account the sizes of the bolt components 8*a* and 8*b* and of the intramedullary nail 4 to be used.

After drilling the bone to the correct diameters, appropriately dimensioned hollow, cylindrical half-bolt components 8*a* and 8*b* are inserted, and the smaller (8*b*) screwed into the larger (8*a*) taking care to maintain correct alignment, especially of the latter. Washer-type plates 15 may be required in some circumstances to improve the hold on the bone, thereby improving compression of vertical fractures through the metaphys. After the bolt components are in place, the intramedullary nail 4 is attached to the rod-like jig member 27 in place of the probe 23, and inserted until the shoulder 27*a* of member 27 again rests against the bone. Once correctly aligned (as checked if necessary with an image intensifier) the grub screws 7*a*, 7*b* are tightened until the nail 4 is securely held in the nail-retaining aperture 3 of the bolt-like fixture means 8.

Figure 8:
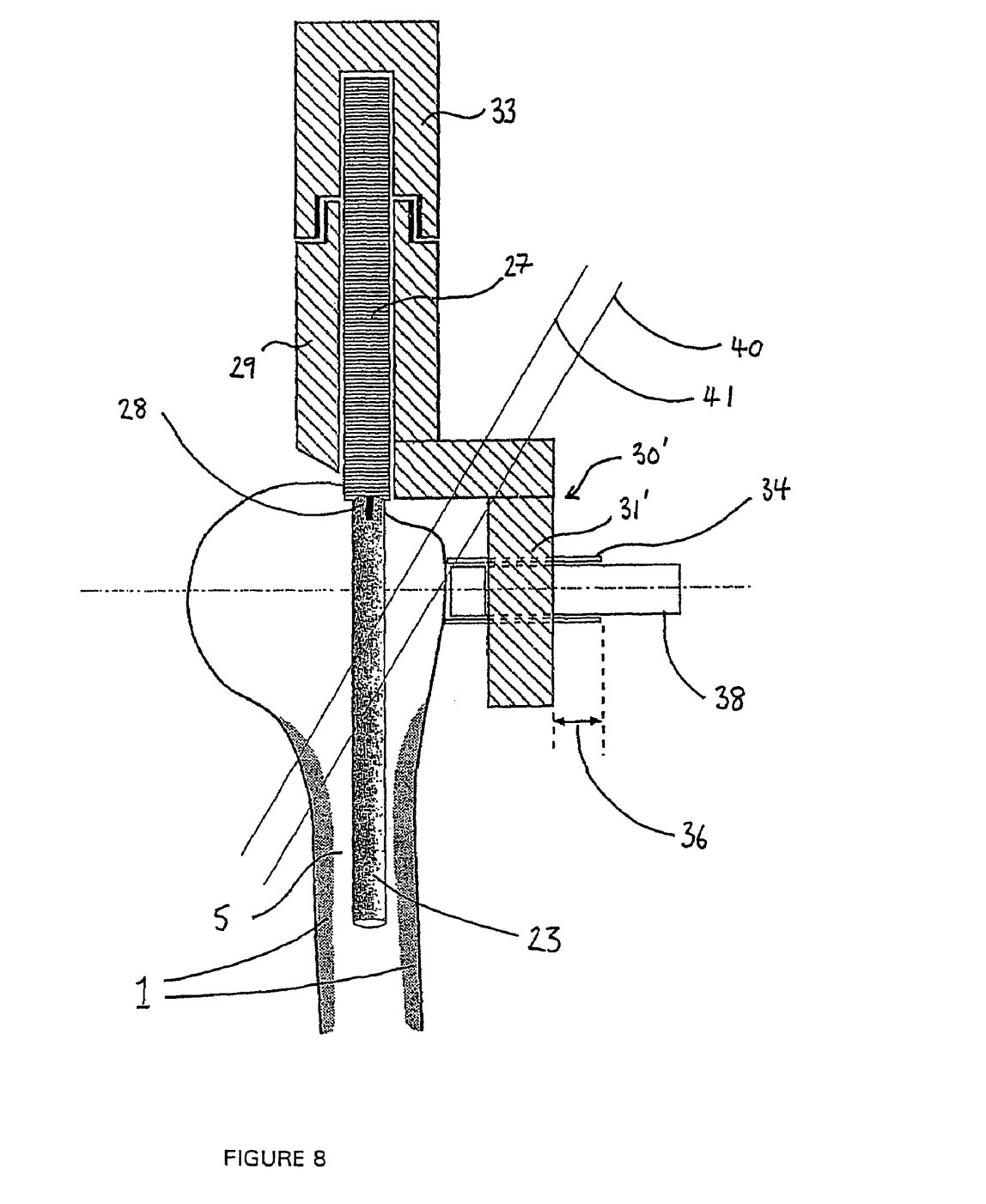
FIGS. 8, 9 and 10 show respective views of a jig arrangement for use with the second and third embodiments of a bone fixture apparatus, in accordance with the invention, described with reference to FIGS. 2 and 3.
Figure 9:
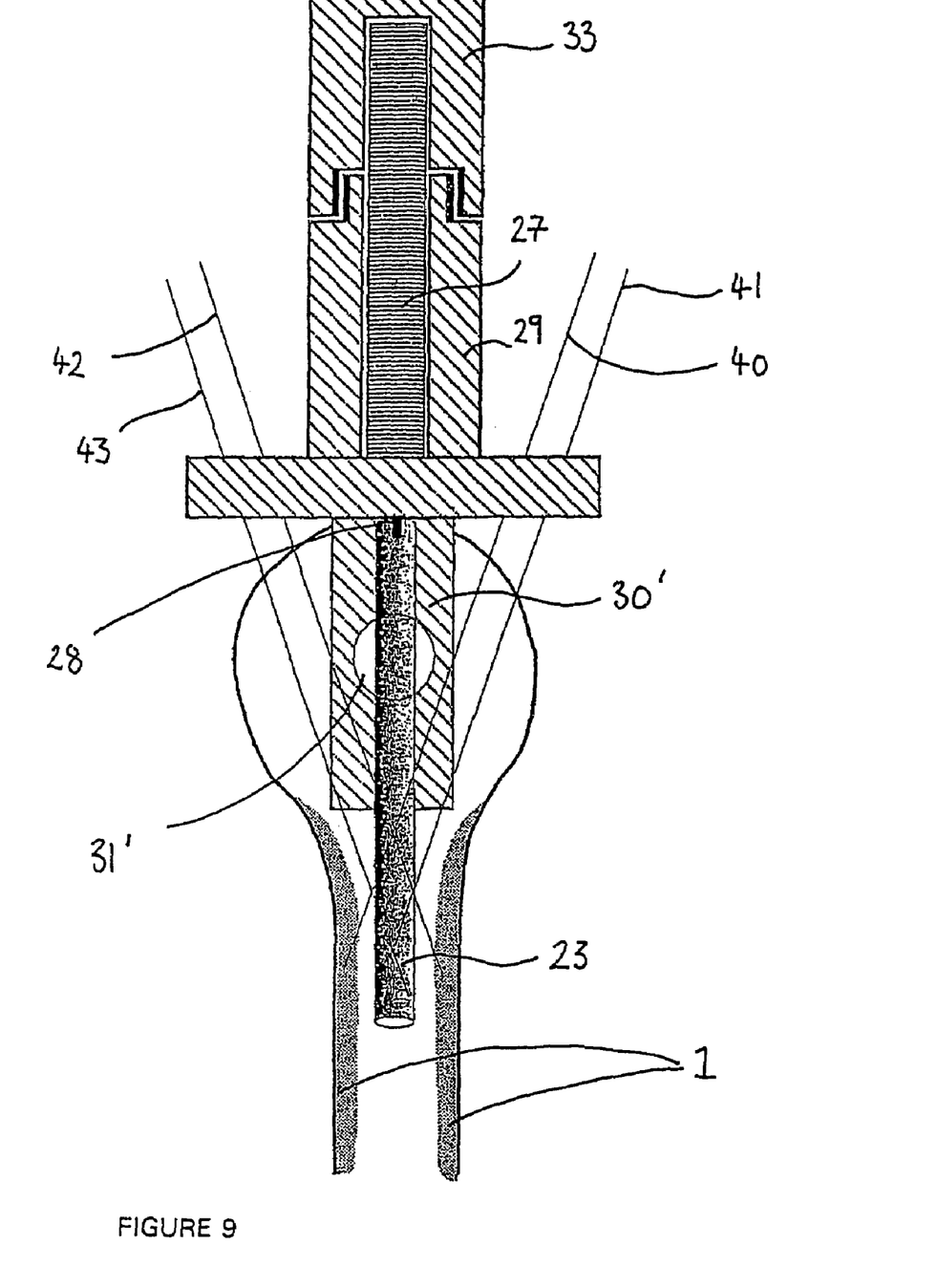
Figure 10:
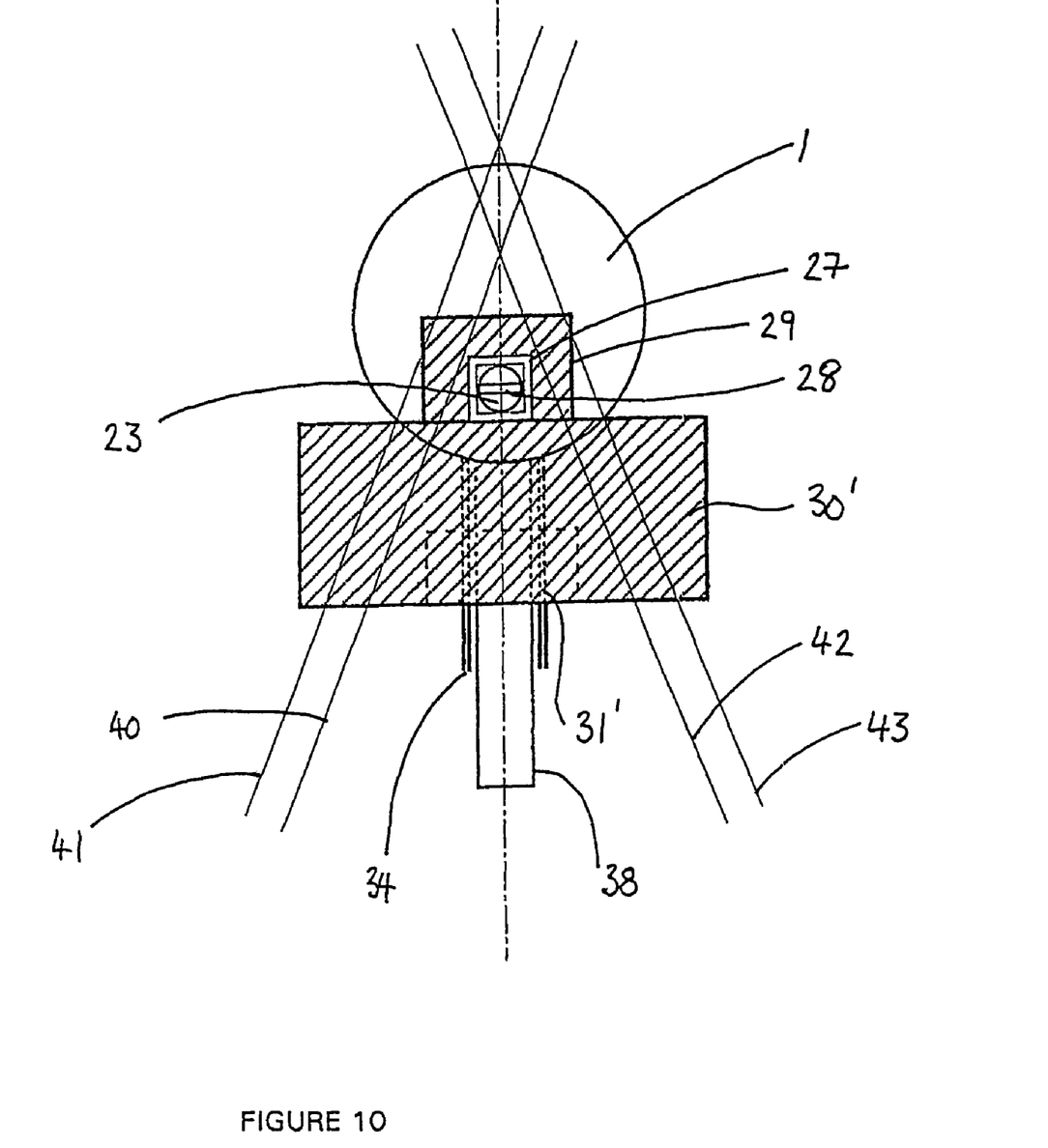

FIGS. 8, 9 and 10 show a jig arrangement suitable for use with the bone fixture apparatus described with reference to FIGS. 2 and 3. This arrangement also makes use of a probe 23 as described with reference to FIG. 4.

The principles of operation and application to the bone of the jig arrangement shown in FIGS. 8 to 10 are similar to those explained above in relation to the arrangement of FIGS. 5 to 7, and thus further detailed explanation will not be given except insofar as it relates to differences in the subject construction and/or procedure.

The sleeve member 29 performs the same function as its counterpart in the arrangement described with reference to FIGS. 5 to 7, but its associated guide member 30' differs from the member 30 described previously in extending only to one side of the bone and being formed with only one drill-guiding aperture 31'.

Once the jig assembly, including a probe 23 as before, has been fixed in place, as described previously, and the positions checked by means of an image intensifier, additional K-wires 40 to 43 are inserted so as to straddle the probe 23. The probe 23 can then be removed, and the appropriate diameter drill inserted through guide aperture 31'; the diameter being selected so as to take into account the intended size of the metaphyseal implant and of the intramedullary device itself.

Sleeves of varying diameters inserted into the guide apertures 31, 32 (FIGS. 5 to 7) and 31' (FIGS. 8 to 10) can usefully be employed to adapt the apertures to accurately accommodate drills and other tools of differing diameters.

The invention claimed is:

1. A bone fixture apparatus for application to a metaphyseal region of a long bone, the apparatus comprising an elongate fixture device intended to be inserted, in said region, in an axial direction generally transversely of a direction of the medullary cavity in said bone; wherein the fixture device includes an aperture extending laterally of said axial direction thereof and intended to accommodate an intramedullary nail inserted longitudinally therethrough into said cavity, and wherein said fixture device is further formed with a bore extending in said axial direction intended to receive a first securing element having a leading surface capable of insertion into the bore to firmly engage an outer surface of the nail and a second securing element having a portion for engaging the fixture device and a head for engaging the bone wherein the fixture device comprises a bolt-like member including first and second components, intended for insertion into a pre-drilled passage in the bone and to engage with cancellous bone to provide a secure fixture which assists in stabilizing a fracture and provides a rigid mount for the intramedullary nail and wherein said first and second components are hollow, cylindrical components of different diameter intended to be inserted coaxially into the bone from opposite directions and adapted to threadably interfit it, within the bone, each component having a threaded bore for receiving a first securing element capable of asserting force again the nail outer surface laterally of the long bone under treatment.

2. Apparatus according to claim 1 wherein at least one of the hollow, cylindrical components of the bolt-like member is formed with said nail-receiving aperture, extending perpendicular to a cylinder axes and intended to accommodate said intramedullary nail inserted therethrough into the medullary cavity of the bone.

3. Apparatus according to claim 2 wherein said first and second cylindrical components are formed with a bore, extending axially therethrough, intended to receive a first securing element for engaging an intramedullary nail sidewall outer surface, when disposed in said nail-receiving aperture, to securely fix the nail to the bolt-like fixture means.

4. Apparatus according to claim 3 wherein said axially extending apertures are screw-threaded and said securing element comprises a grub screw.

5. A bone fixture apparatus for application to a metaphyseal region of a long bone, the apparatus comprising an elongate fixture device intended to be inserted, in said region, in an axial direction generally transversely of a direction of the medullary cavity in said bone; wherein the fixture device includes an aperture extending laterally of said axial direction thereof for receiving an intramedullary nail inserted longitudinally therethrough into said cavity, and wherein said fixture device is further formed with an axial aperture comprising a bore extending in said axial direction intended to receive a securing element with a leading surface capable of insertion therein to firmly engage said nail wherein the fixture device comprises a finned nail-like member, a finned and sharpened distal end of which is intended to be embedded in cancellous bone, wherein the finned, nail-like member is formed with said intramedullary nail-receiving aperture, extending transversely of its longitudinal axis, through which an intramedullary nail can be inserted, wherein the finned, nail-like member is formed with said bore, running axially therethrough, for receiving a locking device for firmly securing said intramedullary nail to the finned, nail-like member wherein said axially extending bore is screw-threaded and said locking device comprises a grub screw.

6. A jig f or inserting a bone fixture apparatus for a permanent intramedullary device into a bone, the jig comprising:
an axially extending elongate insert comprising an intramedullary probe portion and a portion extending out of a bone and including means for releasably connecting the probe portion and the insert portion extending out of the bone; and
a hollow sleeve member having an axially extending bore to receive the elongate insert portion extending from said bone, the hollow sleeve member having a guide portion adapted to extend to at least one side of the bone in use, the guide portion having at least one guide aperture extending orthogonal to the axis of the elongate insert that defines a fixture apparatus insertion axis, said hollow sleeve having a support surface for engaging and being supported by externally facing bone surrounding an intramedullary canal, the jig further comprising a securing means coupled to said elongate insert to limit relative axial movement of the elongate insert portion extending from said bone and the hollow sleeve member in the bore of the sleeve member, the elongate insert is slidably mounted in the base of the hollow sleeve wherein the engagement of a shaped outer surface of the elongate insert and a co-operating inner surface of the bore of the hollow sleeve member prevents rotation of the elongate member in the bore.

7. A jig as claimed in claim 6, wherein the securing means comprises a removable stop means coupled to said elongate insert adapted to limit relative axial movement between the elongate insert and the hollow sleeve member.

8. A jig as claimed in claim 7, wherein the removable stop comprises a cap member adapted for engagement with a proximal end of the hollow sleeve member.

9. A jig as claimed in claim 6, wherein at least part of the elongate insert outer surface has a square cross-section and at least part of the bore of the hollow sleeve member has a co-operating square cross-section.

10. A jig as claimed in claim 6, wherein the elongate insert further comprises a rod portion extending within the base of the hollow sleeve and wherein the intramedullary portion is detachable from the extension portion.

11. A jig as claimed in claim 10, wherein the extension portion is adapted for attachment to a permanent intramedullary device.

12. A method of fixing a permanent intramedullary device to a long bone, comprising:
inserting an elongate insert at least partially into the intramedullary canal of a long bone;
inserting a hollow sleeve member over the elongate insert; using the hollow sleeve member to form an opening in the bone along a fixture apparatus insertion axis generally perpendicular to a long axis of the bone;
withdrawing the elongate insert from the intramedullary canal;
inserting a fixture apparatus into the bone along the fixture apparatus insertion axis;
inserting a permanent intramedullary device into the intramedullary canal and through an aperture in the fixture apparatus; and
applying a force against a sidewall of the intramedullary device and against an outer bone surface surrounding the opening therein via the fixture apparatus.

13. A method as claimed in claim 12, further comprising limiting a relative axial movement between the elongate insert and the hollow sleeve member using a stop element engaging both said insert and the sleeve.

14. A method as claimed in claim 12, wherein the elongate insert comprises an intramedullary portion and a separate extension portion and the method includes the initial step of attaching the intramedullary portion to the extension portion.

15. A method as claimed in claim 14, wherein the step of inserting the permanent intramedullary device includes attaching the permanent intramedullary device to the extension portion of the elongate insert, and using the extension portion to aid the insertion of the permanent intramedullary device into the bone.

16. A method of inserting an intramedullary device through an aperture in a bone fixture apparatus already installed in a bone, including the steps of:
using a hollow sleeve member to define a direction of insertion of the intramedullary device relative to the position of the bone fixture apparatus and form an opening for a bone fixture apparatus in a bone;
attaching an elongate insert to the intramedullary device; inserting the bone fixture apparatus into the bone in a direction generally perpendicular to the direction of insertion; and inserting the intramedullary device and elongate member through the bore in the hollow sleeve member such that the intramedullary device passes through the aperture in the bone fixture apparatus, forceably contacting a sidewall of the intramedullary device with a grub screw in the bone fixture apparatus and forceably contacting an outer surface of the bone surrounding the opening therein with the bone fixture apparatus.

* * * * *